United States Patent [19]

Shigekawa et al.

[11] Patent Number: 5,384,073
[45] Date of Patent: Jan. 24, 1995

[54] LIGAND GOLD BONDING

[75] Inventors: Brian L. Shigekawa, Chapel Hill; Yung-Ao Hsieh, Cary, both of N.C.

[73] Assignee: AKZO N.V., Arnhem, Netherlands

[21] Appl. No.: 185,103

[22] Filed: Jan. 21, 1994

Related U.S. Application Data

[62] Division of Ser. No. 622,462, Dec. 5, 1990, Pat. No. 5,294,369.

[51] Int. Cl.$^6$ ............... B01J 13/00; G01N 33/553; G01N 33/552
[52] U.S. Cl. ............... 252/313.1; 436/525; 436/805; 427/216
[58] Field of Search ............... 252/313.1; 436/525, 436/805; 530/391.5; 427/216

[56] References Cited

U.S. PATENT DOCUMENTS

| | | | |
|---|---|---|---|
| 4,313,734 | 2/1982 | Leuvering | 436/525 |
| 4,744,760 | 5/1988 | Molday | 424/3 |
| 4,859,612 | 8/1989 | Cole et al. | 436/525 X |
| 4,879,220 | 11/1989 | Mrsny et al. | 436/525 X |
| 4,888,248 | 12/1989 | Hirai et al. | 427/216 X |
| 5,147,841 | 9/1992 | Wilcoxon | 252/309 X |
| 5,248,772 | 9/1993 | Siiman et al. | 536/112 |

FOREIGN PATENT DOCUMENTS

WO92/08134 5/1992 WIPO.

OTHER PUBLICATIONS

E. B. Troughton et al., "Monolayer Films Prepared by the Spontaneous Self-Assembly of Symmetrical and Unsymmetrical Diakyl Sulfides from Solution onto Gold Substrates: Structure, Properties, and Reactivity of Constituent Functional Groups", *Langmuir*, vol. 4, No. 2, pp. 364–385, 1988, USA.

M. D. Porter et al., "Spontaneously Organized Molecular Assemblies. 4. Structural Characterization of n-Alkyl Thiol Monolayers on Gold by Optical Ellipsometry, Infrared Spectroscopy, and Electrochemistry", *J. AM. Chem. Soc.*, 1987, 109, pp. 3559–5568, USA.

C. D. Bain et al., "Molecular-Level Control over Surface Order in Self-Assembled Monolayer Films of Thiols on Gold", *Science*, vol. 240, Apr. 1, 1988, pp. 62–63, USA.

A. Ulman et al., "Packing and Molecular Orientation of Alkanethiol Monolayers on Gold Surfaces", *Langmuir*, vol. 5, pp. 1147–1152, 1989, USA.

J. Turkevich et al., "A Study of the Nucleation and Growth Processes in the Synthesis of Colloidal Gold", *Disc. of the Farady Society*, 11, pp. 55–74, 1951, USA.

*Primary Examiner*—Robert L. Stoll
*Assistant Examiner*—John M. Covert
*Attorney, Agent, or Firm*—Mary E. Gormley; William M. Blackstone

[57] ABSTRACT

Gold sol coated with alkanethiols and alkanethiol derivatives, which provide groups on the sol available for the linking of binding moieties such as antibodies, antigens or ligands to the gold sol. Di- and tri-thiol compounds bound to gold sol also facilitate the adsorption of antibodies, antigens or ligands to the sol. The coating process, and test kits incorporating the coated sols are also included.

6 Claims, 8 Drawing Sheets

LIGAND GOLD BONDING

This is a division, of application Ser. No. 07/622,462 filed Dec. 5, 1990, now U.S. Pat. No. 5,249,369.

BACKGROUND

This invention relates to gold sol coated with alkanethiols and alkanethiol derivatives to provide groups on the sol available for the binding or linking of binding moieties such as antibodies, antigens, or ligands to the gold sol. In addition, the use of di- and tri-thiol compounds bound to gold sol facilitate the passive adsorption of these binding moieties. This invention also relates to gold sol coated with thiolated binding moieties, including antigens, antibodies, or carrier molecules, which can be attached to relevant ligands. Also included is the process for coating the gold sols with such thiol compounds, the use of coated sols in immunological and immunocytological diagnostic tests and test kits incorporating such coated gold sols.

Test methods for the diagnosis of various diseases are constantly being improved. Currently, immunological methods are among the most sensitive methods used to detect the presence of antigens or antibodies in samples. These assays are well known to those skilled in the art of immunodiagnostics. Generally, an immunological assay consists of an assay wherein a monoclonal or polyclonal antibody is used to capture an antigen in the sample and a second antibody containing a label, such as a fluorescent compound or an enzyme, immunochemically reacts with the antigen-antibody complex. The resulting labelled antibody-antigen-antibody complex is detected. Variations on this basic assay are common, such as the use of only one reactive antibody in the test, the competitive inhibition method, or the use of particles as labels that allow an agglutination reaction to be read. Another variant is the use of microparticles coated with either an antigen or an antibody, which after formation of a complex with the analyte and a second appropriately labeled binding partner, gives a positive reaction.

Gold sol microparticles are used in an assay method known as a sol particle immunoassay (SPIA). In this assay, a solution containing the gold sol coated with an appropriate binding partner, either an antibody or an antigen, is reacted with a sample to bind to its binding partner. In this process, complexes are formed that can be detected, usually due to their change in color.

Uncoated gold sol particles, and other colloids, will undergo agglomeration when exposed to low concentrations of salt, and quickly precipitate out of solution. Therefore, the coating of gold sol with an appropriate binding partner serves two functions. The first is to provide appropriate immunological binding activity and the second is to protect against agglomeration, which would of necessity occur in buffers designed to optimize for immunological reactions. Since not all proteins or polymers will protect the gold sol completely from salt-induced agglomeration, an overcoating step is usually performed with a protein or polymer that is known to be capable of completely protecting the gold sol from salt-induced agglomeration. Such an overcoating step is a well known practice in adsorbing antibodies and antigens to plastic substrates and has been shown to increase the stability of the coated material.

The overcoating also serves to reduce nonspecific interaction of the gold sol with sample components. This nonspecific interaction is a significant problem when using antibody coated latex particles in diagnostic assays, and is probably a manifestation of the nonspecific serum interference observed in many, if not all, immunoassays, regardless of format. In some cases it is permissible to change the overcoating protein or polymer to minimize interference in specific systems. Additives to the sol medium such as guanidine hydrochloride or urea are useful. Occasionally, "non-specific" interference can be pinpointed to serum heterophile activity and is eliminated by the addition of whole animal serum.

A serious drawback in the passive adsorption of the desired binding partner to gold colloid has been that such direct coating is often unsuccessful. The physicochemical mechanisms of passive polymer adsorption to colloids in general is a poorly understood process. Passive adsorption of antibodies to gold sol may result in a coated sol which is poorly protected from salt-induced agglomeration and which cannot be further protected by overcoating. It may also result in a coated sol with poor immunological activity, presumably due to the incorrect orientation of adsorbed antibody, or it may result in the antibody-induced agglomeration of the sol itself. Finally, the binding partner of choice may simply not bind to the gold sol. The net result of these problems is that few biological reagents useful in other diagnostic formats can be used in the production of gold colloid reagents of diagnostic quality.

What is needed in the art is a method for covalently attaching binding partners, proteins, carbohydrates or ligands, to the gold sol so that the uncertainties of the passive adsorption characteristics or the necessity of making binding partner and "good coating" carrier conjugates for passive adsorption may be eliminated. In particular, such a sol would be significantly more useful if it were refractive to salt-induced agglomeration even in the absence of a coated binding partner. The ability to change the physico-chemical surface properties of the sol would, at the same time, make it possible to minimize the sometimes undefined sample-sol interactions responsible for non-specific interference in immunochemical diagnostic assays and background problems in immunocytochemical assays.

What is also needed is the ability to facilitate the passive adsorption of biological polymers to gold sols. Thiolation of antibodies and polymers can increase their ability to bind to gold sols as evidenced by increased resistance to salt-induced agglomeration. Such a capability may prove useful for those antibodies which bind well to gold sols, but lose significant amounts of their activity in doing so as well as for antibodies which simply do not bind the gold sol in an underivatized state. An alternative method of changing the physicochemical characteristics of the sol surface in order to facilitate antibody binding is the coating of the sol with di-thiol or tri-thiol compounds. Such an intermediate coating can significantly change the passive adsorption properties of antibodies to the coated sol.

SUMMARY OF THE INVENTION

This invention provides a process for coating microparticles of gold sol with alkanethiols, alkanethiol derivatives, and di- and tri-thiol compounds. Gold sols coated with alkanethiols or their derivatives are resistant to salt-induced agglomeration and contain chemical moieties for covalent polymer or ligand attachment.

A particular hydrophobic-hydrophilic balance of the sol surface is obtained and nonspecific interactions of the sol with proteins generally are minimized. In particular, chemical groups distal to the n-alkane thiol moiety, such as methyl, hydroxyl, carboxyl, amino, sulfhydryl or carbonyl, are solvent exposed and serve as covalent attachment sites and may be hydrophobic-hydrophilic balance sites.

Coating gold sol with small molecular weight di- and tri-thiol compounds does not protect the sol from salt-induced agglomeration, but changes the physico-chemical nature of the coated sol surface and facilitates the passive adsorption of antibody molecules.

Also included in the present invention is the coated gold sol. The invention also includes coated gold sol particles additionally bound to binding moieties such as antibodies or antigens and diagnostic kits containing said gold sol particles.

Lastly, the invention includes coated gold sols to which binding moieties are attached by adsorption, and uncoated gold sol where adsorption is facilitated through the thiolation of the binding moiety.

DETAILED DESCRIPTION OF THE INVENTION

Figure 1:
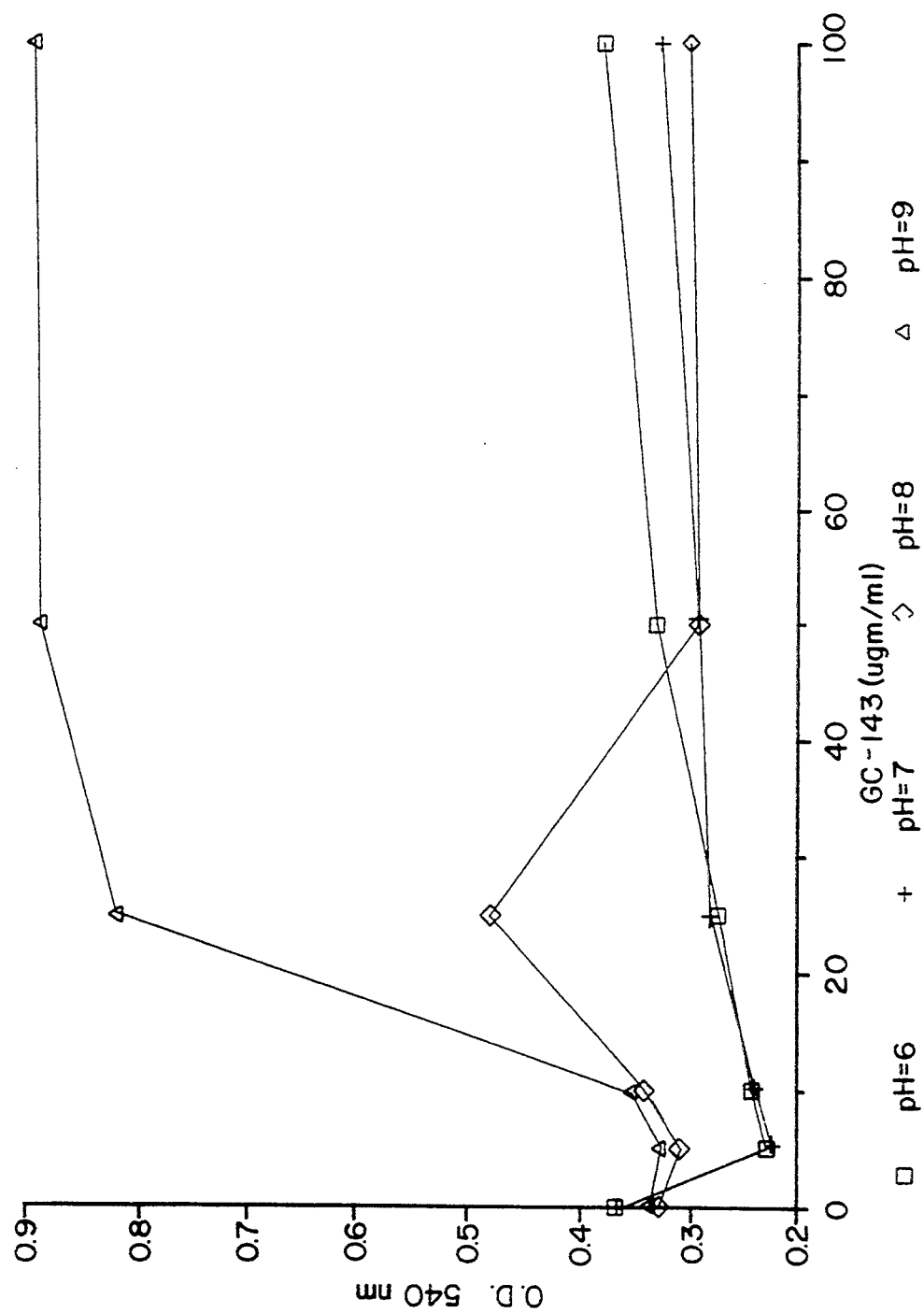
FIG. 1 demonstrates the relative resistance to salt-induced gold sol agglomeration conferred by coating the gold sol with anti-gp160 antibody (GC-143) at various concentrations and pH values.
Figure 2:
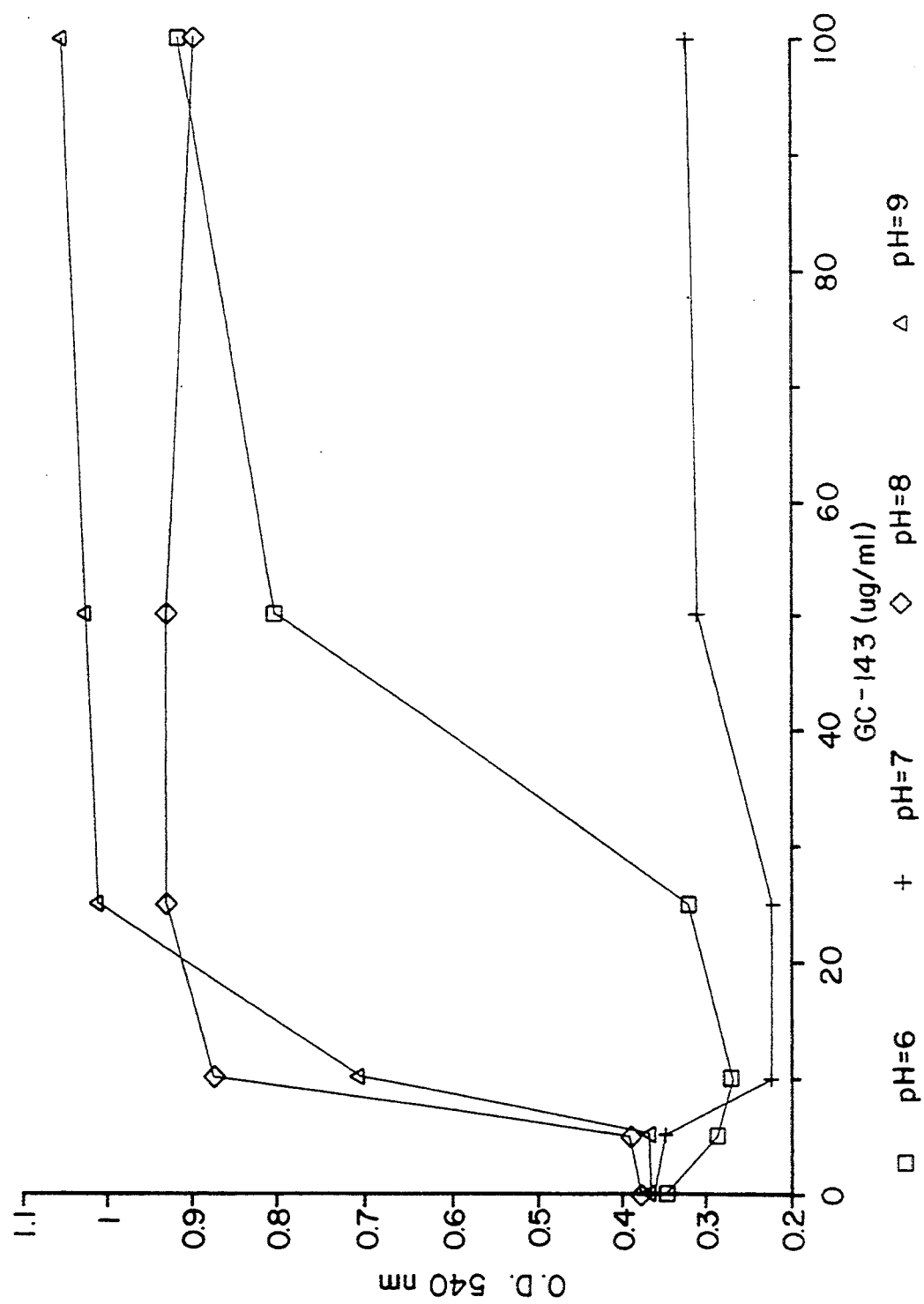
FIG. 2 demonstrates the relative resistance to salt-induced gold sol agglomeration conferred by coating a TTC coated gold sol with anti-gp160 antibody (GC-143) at various concentrations and pH values.
Figure 3:
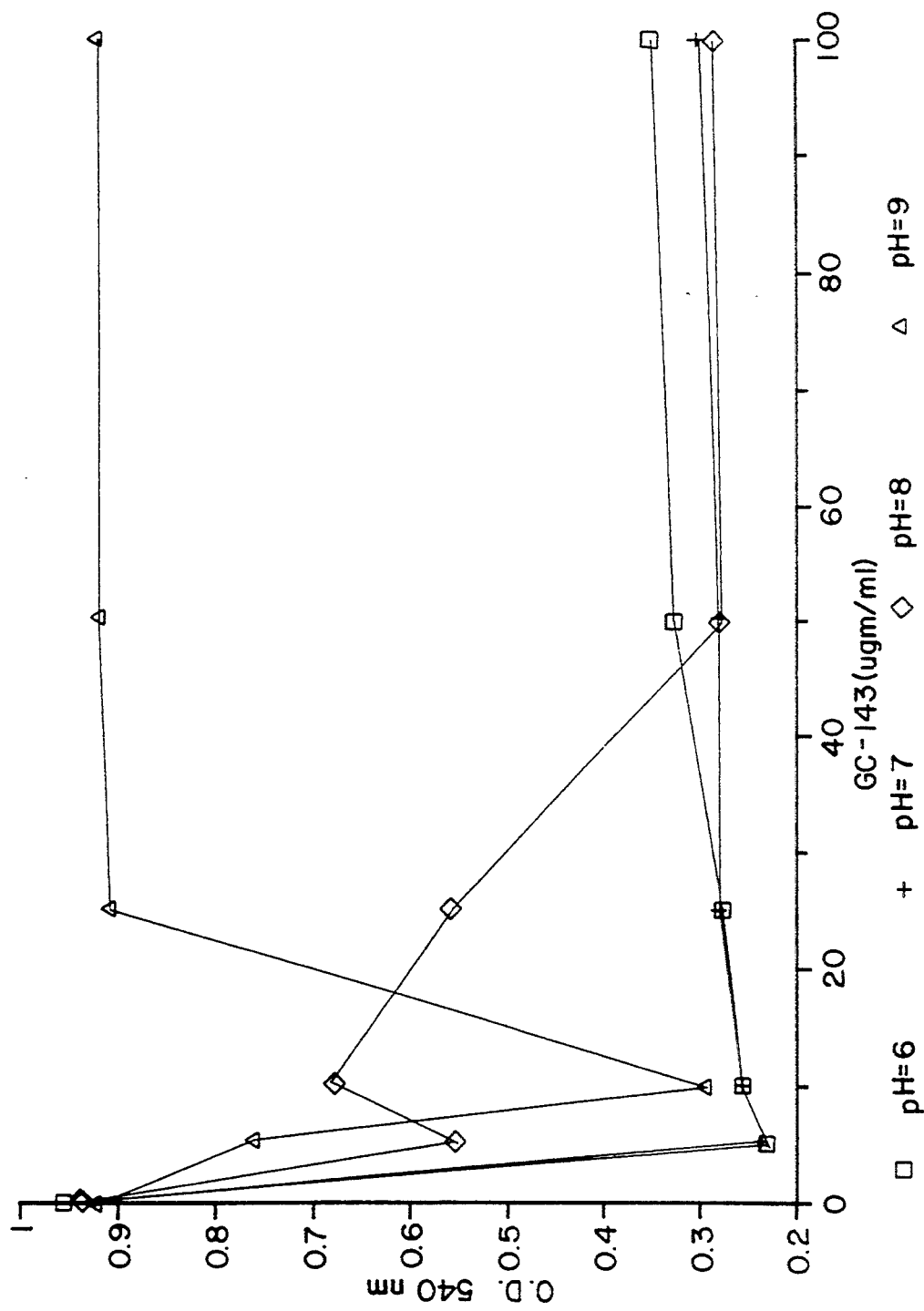
FIG. 3 demonstrates the ability of GC-143 to cause spontaneous agglomeration of a gold sol in the absence of any added salt at various concentrations and pH levels.
Figure 4:
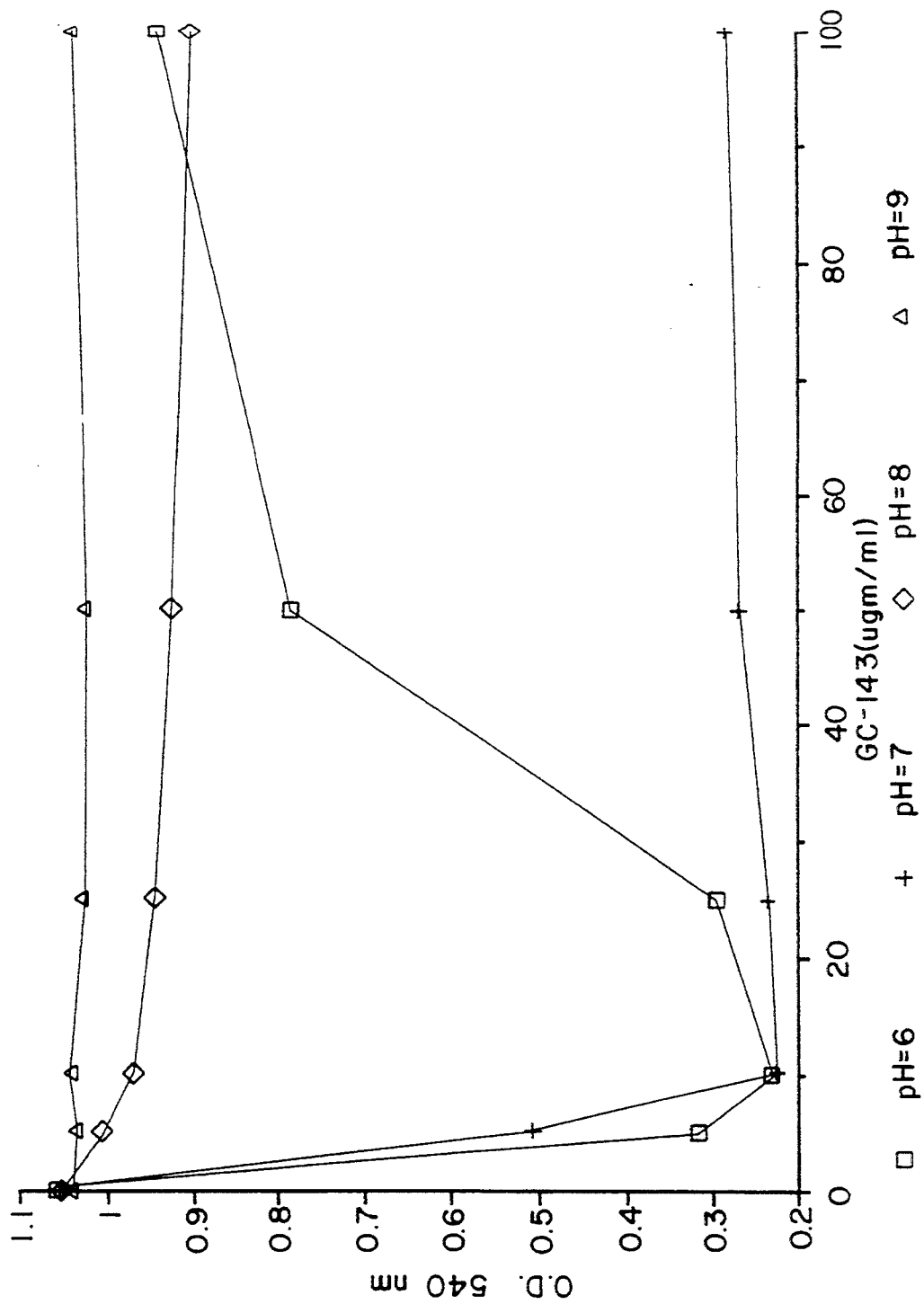
FIG. 4 demonstrates the ability of GC-143 to cause spontaneous agglomeration of a TTC coated gold sol in the absence of any added salt at various concentrations and pH levels.

The process of coating microparticles consisting of gold sol to provide chemical linking groups to facilitate the further attachment of other groups is the basis of the present invention. Microparticles in the invention are generally defined as colloidal gold sol that range in size from about 20 nm to about 200 nm or more. The preferred range of microparticle is from about 60 to about 80 nm. The most preferred size is about 65 to 75 nm. Some of the coating chemicals used, such as alkanethiols and their derivatives and mixtures thereof also protect the gold sols from salt-induced agglomeration and may produce a particular hydrophobic-hydrophilic balance of the sol surface so that nonspecific interactions of the surface with extraneous proteins are minimized.

Gold sol was produced by the hydroxylamine-mediated reduction of chloroauric acid in water onto seed gold particles. This procedure is described in the literature. (Turkevich, J. et al., Discussions of the Faraday Society, No. 11, p. 55-74 (1951)). Generally, chloroauric acid trihydrate dissolved in water is added to deionized water, to which is then added hydroxylamine hydrochloride. Seed gold particles are added and stirred. A small amount of acetone is added, and the mixture is stirred. $K_2CO_3$ is added until the pH reaches 7.0. The gold sol ranges in size from about 20 nm to about 150 nm in diameter depending on the amounts of gold particle added and the amount of chlorauric acid used, and is now ready to be coated with alkanethiols or thiol derivatives.

Alkanethiols, their derivatives, and di- and tri-thiol compounds are the preferred compounds used to coat the gold sol particle and to provide chemical moieties or linking groups for covalent polymer or ligand attachment to the gold sol or for the modification of the hydrophilic/hydrophobic balance. The more preferred are the n-alkanethiols, while the most preferred compounds are alkanethiols of the formula $CH_3(CH_2)_nSH$, where n equals 9 to 23. Derivatives of the alkanethiols are generally of the formula $RCH_2(CH_2)_nSH$ wherein R is OH, COOH, CHO, SH and $NH_2$, and n is 9 to 23. The di- and tri-thiol compounds are generally compounds of low molecular weight. Some of them have been recognized as heavy metal chelators. Two examples are 2,3-dimercaptosuccinic acid and trithiocyanuric acid.

To coat a sol with an n-alkanethiol, 0.10M of the alkanethiol and 1% Tween-20 ® (ICI Americas registered trademark, polyoxyethylenesorbitan monolaurate) in alcohol, preferably methanol, is freshly prepared. Approximately 1 ml of this mixture is added to approximately 100 ml of the prepared gold sol, and is stirred. The resulting mixture is allowed to set at room temperature for approximately 2 hours. Lower concentrations of the coating compound will effectively coat gold sol but the optimal coating times must be found empirically for each case.

The sol mixture is washed into an approximately 1 mM 3-[N-Morpholino]-2hydroxypropane sulfonic acid (MOPSO), pH 7 buffer by centrifugation at 2000×g for approximately 15 minutes at room temperature, and can be stored at 4° C. until use.

The above is an example of coating gold sol with an n-alkanethiol compound. This coating procedure is modified for the attachment of mixtures of n-alkanethiols and n-alkanethiol derivatives containing linking groups for the chemical conjugation of ligands, or polymeric compounds. For example, the inclusion of an hydroxy-n-alkanethiol to the coating mixture increases the hydrophilicity of the sol surface and decreases the non-specific interaction of the sol with serum proteins. The inclusion of a carboxyl-n-alkanethiol at a level of 10% of total thiol compounds present is sufficient to produce a sol with the desired density of conjugation moieties. The carbon chain length of the n-alkanethiol in these mixtures can be 2-4 carbons less than the carbon chain length of the n-alkanethiol derivatives in order to better expose the conjugation moieties to reduce steric hindrance associated with reaction of macromolecules with the sol surface.

The coating solution of n-alkanethiol, n-alkanethiol derivative or mixtures of the two groups is generally made in alcohol, preferably methanol, with 1% Tween-20 ®. The total concentration of all the thiol compounds is generally no greater than 0.10M. In some cases, the optimal pH for coating thiol compounds is not 7. For example, in the case of trithiocyanuric acid coated sols, the sol is adjusted to pH 6 before the addition of the thiol compound to optimize the degree of resistance to salt-induced agglomeration conferred by a particular thiol compound mixture.

The sols are generally allowed to coat in the presence of the thiol mixture for 2 hours, but optimal incubation times are determined empirically for each case. This is accomplished by testing the sols for their resistance to salt-induced agglomeration after incubation periods of varying length using a spectrophotometric assay. Gold sols have a characteristic violet color, which is exceedingly sensitive to the diameter of the sol particles. If sol particle agglomeration takes place, the effective "size" of the sol is greatly increased and the characteristic absorption maximum shifts from 540 nm, which is violet, to higher wavelengths, with a blue to colorless sol color.

In practice, 1 ml of the coated sol aliquot is dispensed into a glass tube. One hundred microliters of 10% NaCl are added to the sol aliquot with mixing. The mixture is allowed to set at ambient temperature for 10 minutes and its absorbance at 540 nm is compared to an identical sol aliquot to which 100 microliters of water have been added. A test aliquot that retains 90% or greater of the absorbance of the control aliquot is considered to be resistant to salt-induced agglomeration.

Compounds tested are shown in Table 1 below.

TABLE 1

| Compound(s) | Relative Degree of Protection From Salt-Induced Agglomeration* |
|---|---|
| n-hexadecanethiol | 97% |
| n-dodecanethiol | 93% |
| n-hexadecane | 25% |
| 1-hexadecanoic acid | 26% |
| 12-mercapto-1-dodecanoic acid | 46% |
| 11-mercapto-1-undecanol | —[1] |
| 2,3-dimercapto succinic acid | 41% |
| 2,5-dimercapto-1,3,4-thiadiazole | 94%[2] |
| 3-amino-5-mercapto-1,2,4-triazole | <30% |
| trithiocyanuric acid | <30% |
| n-dodecanethiol: 12-mercaptododecanoic acid | |
| (1:1)[3] | 74% |
| (4:1) | 76% |
| (9:1) | 90% |
| n-decanethiol:11-mercapto-1-undecanol: 12 mercapto dodecanoic acid | |
| (8:1:1) | 100% |
| (6:3:1) | 83% |

*expressed as % optical density at 540 nm of control sol aliquot with no added salt.
[1]the sol was spontaneously agglomerated in the presence of the coating compound
[2]even though the sol was protected from salt-induced agglomeration, after harvesting by centrifugation the sol was no longer salt protected.
[3]mole ratios of compounds used in coating mixtures The compounds found to be most successful in coating the gold sol and protecting it from salt-induced agglomeration were n-alkanethiols. N-alkanethiol derivatives such as 12-mercapto-1-dodecanoic acid were ineffective by themselves in conferring resistance to salt-induced agglomeration, but sols coated with mixtures of n-alkanethiols and their derivatives did confer complete protection from salt-induced agglomeration and contributed the other properties discussed above.

The coated gold sol containing chemically conjugatable groups is then bound to binding moieties such as proteins, carbohydrates, antibodies, antigens, polymers, monomers or ligands using carbodiimide chemistry by well known methods. Binding moieties include any groups that are capable of being adsorbed or covalently attached to the coated gold sol. In some cases, carbodiimide chemistry is also used to conjugate a linker molecule such as 6-amino caproic acid to the sol prior to the indirect conjugation of the binding partner in order to relieve steric constraints on the binding partner and aid in its recognition by and of its complementary binding partner. In order to conjugate the binding partner or the linker molecule to the coated sol, the sol is incubated at ambient temperature in the presence of the substance to be coupled, 1-ethyl-3-(3-dimethylaminopropyl)carbodiimide hydrochloride(EDC), and N-hydroxysulfosuccinimide(SNHS), in a 10–25 mM buffer at pH 7.0 for 2 hours. In some cases, sequential aliquots of EDC are added during the conjugation reaction in order to compensate for the hydrolysis of this compound in aqueous media.

The choice of potentially useful conjugation chemistries is determined by the chemical moiety on the coated sol as well as by the type of moiety introduced on any given linker molecule. For example, amino groups on the sol-bound alkanethiol derivatives or attached linker molecules could be conjugated to polymers using homo- or hetero-bifunctional N-hydroxysuccinimide ester crosslinkers. Likewise, sulfhydryl groups on sol-bound alkanethiol derivatives or linker molecules could be conjugated to polymers using homo- or hetero-bifunctional maleimide crosslinkers. The range of possible conjugation schemes is very similar, if not identical to, the range of chemical schemes currently used in the preparation of diagnostic immunoconjugates. Classical crosslinking reagents compatible with the moieties on the sol, the alkanethiol derivatives or the chemical crosslinkers are needed to attach the appropriate binding partner to the sol.

Immunoassays using the sol particle immunoassay (SPIA) method are performed as described in J. Leuvering U.S. Pat. No. 4,313,734. Briefly, gold sol coated with a binding moiety is incubated in the presence of a test sample containing the opposite binding partner. If the opposite binding partner is present in the sample, cross linking of the coated sol will result and the absorbance at the absorption maximum of single gold sol particles will decrease dramatically. The adsorption properties of polymeric compounds to gold sols may be facilitated by the thiolation of the binding partner.

Figure 7:
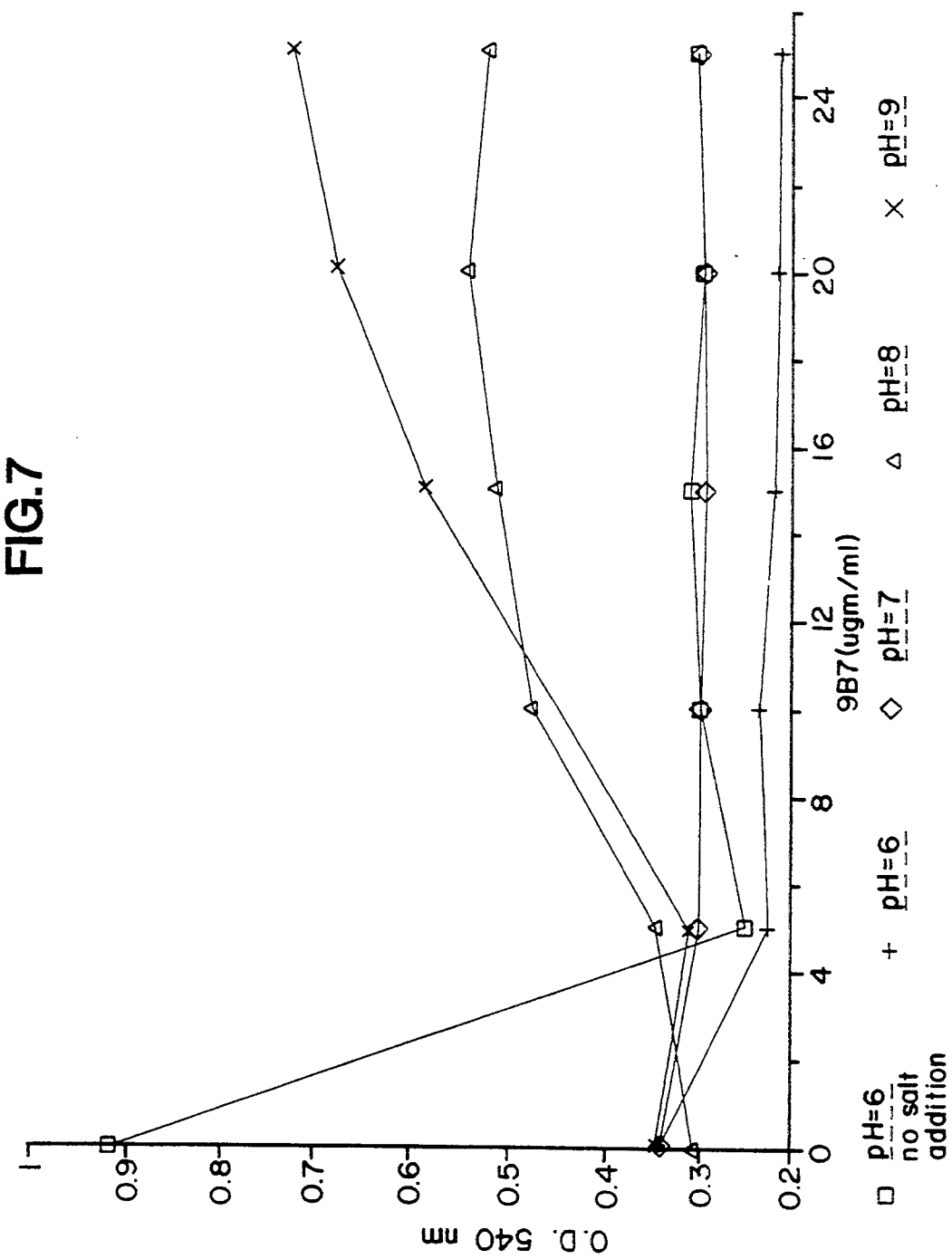
FIG. 7 demonstrates the ability of an underivatized monoclonal anti-HIV p24 antibody adsorbed to gold sol to protect the sol from salt-induced agglomeration.
Figure 8:
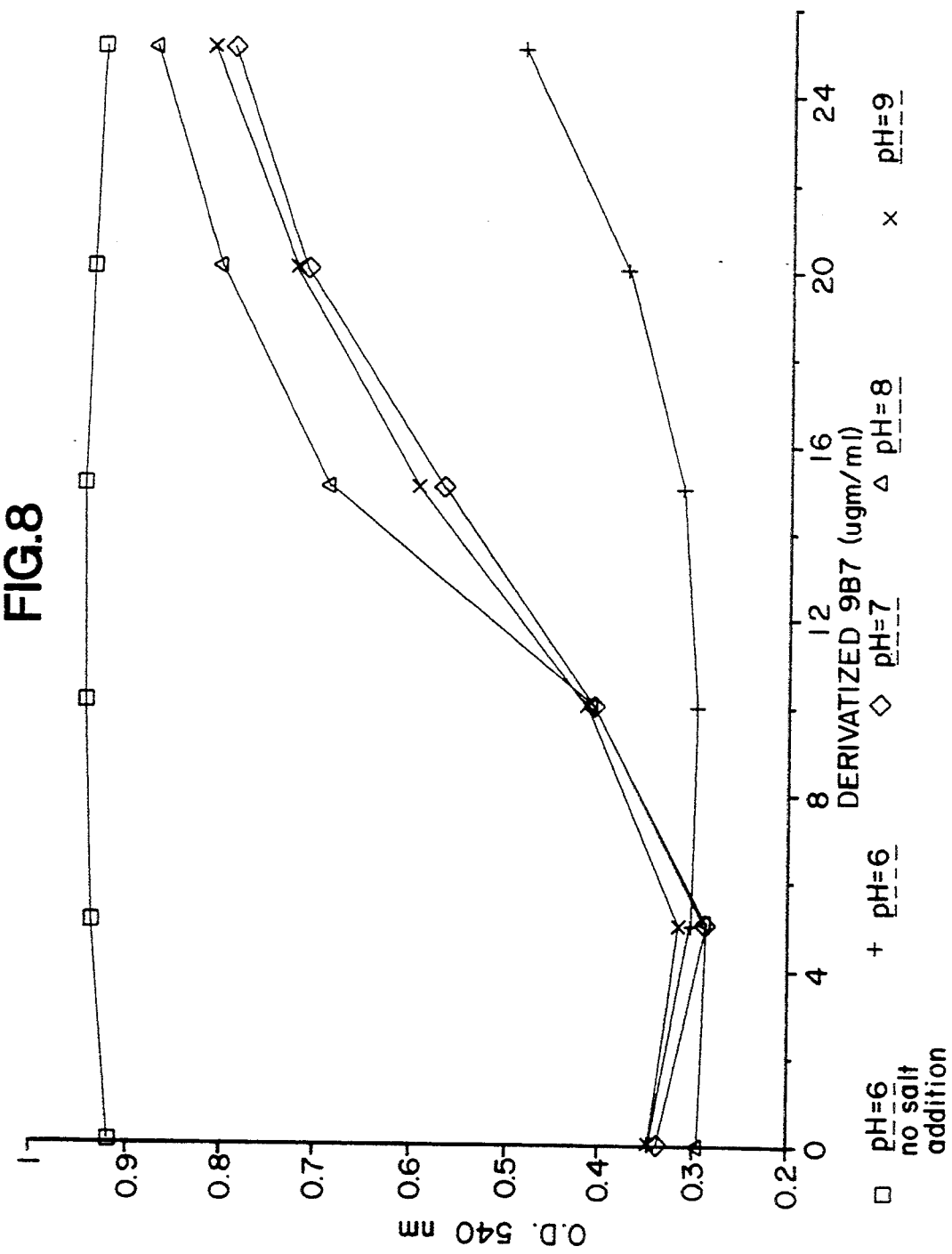
FIG. 8 demonstrates the ability of thiolated monoclonal anti-HIV p24 antibody adsorbed to gold sol to protect the sol from salt-induced agglomeration.

Both polyclonal and monoclonal antibodies were thiolated by reaction with N-succinimidyl S-acetylthioacetate (SATA). The resulting protected sulfhydryl groups were exposed by reaction of the proteins with hydroxylamine hydrochloride. This is a well known chemical procedure for introducing sulfhydryl groups into protein. The thiolated proteins were then adsorbed to gold sols at pH's 6, 7, 8 and 9 at protein concentrations ranging from 5 µg/ml to 100 µg/ml. The degree of resistance to salt-induced agglomeration was determined as described above. Thiolation of antibodies by this method significantly improved their ability to protect gold sol from salt-induced agglomeration over non-thiolated antibodies, as shown in FIGS. 7 and 8, and described in Example 12.

An alternative method of facilitating the adsorption of antibodies to gold sol is the inclusion of an intermediate coating between the gold sol and the binding partner in order to change the physico-chemical properties of the sol surface such that adsorption of the antibodies is increased. Di- and tri-thiols are used for such a purpose. Trithiocyanuric acid (TTC) is an example of such a compound. Gold sol was coated with TTC in a procedure similar to that described above for the n-alkanethiol compounds but with different concentrations of TTC and Tween-20®. These concentrations were determined empirically. The ability of antibody to confer resistance to salt-induced agglomeration of the washed sol was determined after incubation of the antibody and the coated sol at various pH's and protein concentrations in the previous paragraph.

The coated microparticles of this invention may be covalently bound to antigen or antibodies and sold in a test kit for use in immunodiagnostics. The antigen or antibody will be specific for the opposite binding partner sought to be detected, and the other components of the kits may include diluents, buffers, labeling reagents and laboratory equipment that will also be specific for the particular test to be performed.

The following examples are given to more fully explain, but not to limit the invention. Modifications of the invention will be obvious to those skilled in the art and are also considered as part of this invention.

EXAMPLES

EXAMPLE 1

Preparation of Gold Sol

For preparation of the seed sol used in the final gold sol preparation, 10ml of 1% HAuCl$_4$ trihydrate was added to 900 ml of water and stirred well. 10 ml of 1% sodium citrate was added to the mixture and stirred well. With vigorous stirring, 10ml of 0.075% sodium borohydride was added (made by dissolving sodium borohydride in the sodium citrate solution) and stirred well for 5 minutes. The mixture was filtered through a 0.22 micron filter and stored at 4° C. The sol should age at least 24 hours before use.

For preparation of the final gold sol, 8 ml of 2% HAuCl$_4$ trihydrate (in water) was added to 900 ml of water. With continuous stirring, 4 ml of freshly prepared 5% hydroxylamine hydrochloride was added (in water). Immediately thereafter, 22.33 microliters of seed sol was added and stirred vigorously for 30 minutes. 1 microliter of acetone was added for each milliliter of sol produced and stirring continued for 10 minutes. 0.2M K$_2$KCO$_3$ was added until the desired pH was obtained.

The appropriate volume of seed sol added was determined by the following relationship: Volume of seed required for desired sol size=Volume of seed required for sol of given size times the cube root of (Diameter of sol obtained from a given amount of seed sol divided by diameter of the desired particle).

EXAMPLE 2

Coating of Gold Sol with n-Alkanethiol

Gold sol was prepared as described in Example 1. A solution of 0.1M 1-dodecanethiol in methanol and 1% Tween-20 ® was freshly prepared. For every 100 ml of gold sol to be coated, 1 ml of the thiol-methanol solution was added dropwise with stirring to the gold sol. The mixture was allowed to set at ambient temperature with occasional swirling for 2 hours. The coated gold sol was recovered by centrifugation at 2000×g for 15 minutes at ambient temperature with subsequent resuspension in 1 mM MOPSO, pH 7.0. This centrifugation and resuspension was repeated 3 times. The resultant sol was resuspended in the same buffer and stored at 4° C. prior to use.

EXAMPLE 3

A n-Alkanethiol and n-Alkanethiol Derivative Mixture Coated Gold Sol

Gold sol was prepared as described in Example 1. A solution of 0.09M 1-dodecanethiol, 0.01M 12-mercapto-1-dodecanoic acid in methanol and 1% Tween-20 ® was freshly prepared. For every 100 ml of gold sol to be coated, one ml of the thiol mixture-methanol solution was added dropwise with stirring to the gold sol. The mixture was allowed to set at ambient temperature with occasional swirling for 2 hours. The coated gold sol was recovered in a manner identical to the previous example.

EXAMPLE 4 n-Alkanethiol Derivative Gold Sol Coating and Subsequent Lack of protection from Salt-Induced Agglomeration Gold sol was prepared as described in Example 1 and adjusted to ph 7 with K$_2$CO$_3$. A solution of 0.10M 12-mercapto-1-dodecanoic acid and 1% Tween-20 ® in methanol was freshly prepared. For every 100 ml of gold sol to be coated, 1 ml of the thiol-methanol solution was added dropwise with stirring to the gold sol. The mixture was allowed to set at ambient temperature with occasional swirling for 1 hour. To duplicate 1 ml aliquots of the coated sol were added either 100 $\mu$l of water or 10% NaCl. The aliquot to which water was added was considered the control. The aliquot to which 10% NaCl was added had lost 54% of its optical density after 10 minutes. This is interpreted as evidence that the gold sol was not protected from salt-induced agglomeration by being coated with the 12-mercapto-1-dodecanoic acid.

EXAMPLE 5

Preparation of a Gold Sol Coated with a Mixture of n-Alkanethiol and n-Alkanethiol Derivatives Gold sol was prepared as described in Example 1 and adjusted to pH 7 with K$_2$CO$_3$. A solution of 0.004M N-decanethiol, 0.0005M 11-mercapto-1-undecanol, 0.0005M 12-mercapto-1-dodecanoic acid, 0.08M NaCl and 1% Tween-20 ® in methanol was freshly prepared. For every 100 ml of sol to be coated, 1 ml of the thiol-thiol derivative solution was added dropwise with stirring and the mixture was allowed to set overnight at ambient temperature. The coated sol was assayed for protection from salt-induced agglomeration as in Example 4.

The coated sol retained 100% of its optical density at 540 nm after the addition of 10% NaCl. This is believed to show that the coated sol is fully protected from salt-induced agglomeration.

EXAMPLE 6

Bovine Serum Albumin (BSA) Conjugation to Coated Gold Sol

Four ml of the coated gold sol described in Example 3 with an optical density at 540 nm of 25.0 was mixed with 4.3 ml of 10 mM MOPSO, pH 7.0. To this mixture was added sequentially with stirring, 0.2 ml of 25 mg/ml BSA, 1.0 ml of 30 nm SNHS, and 0.5 ml of 0.1M EDC. The BSA, SNHS and EDS were prepared in 10 mM MOPSO, pH 7.0. The reaction was rocked for 2 hours at ambient temperature. The reaction was quenched by an additional hour of rocking after the addition of 1 ml of 1.0M ethanolamine (adjusted to pH 7.0 with HCl), pH 7.0 in 10 mM MOPSO. An equal volume of 10 mM MOPSO, 0.15M NaCl, 0.5% Tween-20®, 1.0 mg/ml casein, at pH 7.0 was added to the reaction mixture and the mixture was allowed to set for 1 hour. This blocking or overcoating step protects the unreacted bare areas of the gold sol surface from non-specific interaction with other biopolymers. The BSA conjugated coated sol was recovered by centrifugation at 2000×g at ambient temperature for 15 minutes and subsequent resuspension in the same buffer. This centrifugation and wash was repeated 3 times. The sol was centrifuged as above and resuspended in 10 mM MOPSO, pH 7.0. This step was repeated twice. The BSA conjugated coated sol was stored at 4° C. prior to use.

EXAMPLE 7

SPIA of PSA Conjugated Gold Sol

The BSA conjugated gold sol from Example 5 was diluted in 0.1M MOPSO, 0.15M NaCl, 1.0% polyethylene glycol 8000, pH 7.0 to obtain an optical density at 540 nm of 1.0. Polyclonal anti-BSA antibody and normal rabbit immunoglobulin(IgG) were diluted in 10 mM MOPSO, pH 7.0 to 12 microliters/ml. To separate 1 ml aliquots of BSA conjugated sol were added 100 microliters of the diluted anti-BSA or normal rabbit IgG, or 10 mM MOPSO buffer with mixing. The mixtures were transferred to cuvettes and the optical densities at 540 nm were monitored over time and shown in Table 2.

The results in Table 2 demonstrate that there is immunologically recognizable BSA on the surface of the sol and that the decrease in optical density is not due to nonspecific interaction of rabbit serum with the sol.

EXAMPLE 8

SPIA of BSA Negative Control Conjugated Gold Sol

A negative control BSA conjugated coated sol was prepared exactly as in Example 5 above except that no EDC was added to the conjugation reaction. An identical volume of 10 mM MOPSO, pH 7.0 buffer was included instead. The purpose of this sol was to demonstrate in SPIA assays that the BSA activity observed was covalent in nature. Comparison of results in Tables 2 and 3 demonstrate that although a significant portion of the BSA activity on these sols may be passively adsorbed, an equally significant portion is covalently bound.

TABLE 2

| SAMPLE | BSA CONJUGATED COATED SOL DECREASE IN O.D. 540 nm AT 60' |
| --- | --- |
| Anti-BSA | 0.401 |
| Rabbit IgG | 0.029 |
| Buffer | 0.031 |

TABLE 3

| SAMPLE | BSA NEGATIVE CONTROL CONJUGATED GOLD SOL DECREASE IN O.D. 540 nm AT 60' |
| --- | --- |
| Anti-BSA | 0.238 |
| Rabbit IgG | 0.063 |
| Buffer | 0.050 |

EXAMPLE 9

Improvement in Coating Properties of Antibody on TTC Coated Gold Sol

Gold sol was prepared as described in Example 1, except that its pH was adjusted to 6.0 with $K_2CO_3$. A saturated solution of TTC in methanol was freshly prepared. A solution of 10% Tween-20® in methanol was added until the final Tween20® concentration was 2.5%. Four ml of this solution was added to 200 ml of the above sol with stirring and the mixture was allowed to set at ambient temperature for 2 hours with occasional swirling. The coated sol was harvested as in Example 2. Separate aliquots of the coated sol were diluted to an optical density of 2.0 and simultaneously adjusted to pH 6, 7, 8 and 9 with 10 mM (2-[N-morpholino]ethanesulfonic acid) (MES), 10 mM MOPSO, 10 mM (N-[2-hydroxethyl]-piperazine-N-[3-propanesulfonic acid]) (EPPS), and 10 mM (2-[N-cyclohexylamino]-ethanesulfonic acid) (CHES), respectively. In parallel, a gold sol was prepared as in Example 1 and separate aliquots were adjusted to pH 6, 7, 8 and 9 with $K_2CO_3$. A purified human anti-HIV polyclonal antibody was diluted to 1.0, 0.5, 0.25, 0.10 and 0.05 mg/ml in each of the above buffers. To parallel 1.0 ml aliquots of each of the above sols and each pH was added 100 μl of antibody solution at the corresponding pH with mixing. The mixtures were allowed to set at ambient temperature for 30 minutes. One hundred μl of 10% NaCl was added to each sol mixture with agitation. After an additional 10 minutes, the optical density at 540 nm of each mixture was measured, as shown in FIGS. 1–4.

The adsorption of the antibody on the TTC coated sol resulted in a broader pH range at which protection from salt-induced agglomeration occurred. Also, protection from salt-induced agglomeration took place at lower antibody concentrations on the TTC coated sol. In the absence of NaCl addition, the antibody caused spontaneous agglomeration of the uncoated sol. The antibody-induced spontaneous agglomeration was much less apparent on the TTC coated sol.

Collectively, these observations show that the adsorption of this antibody on TTC coated gold sol is greater than that seen on uncoated sol.

EXAMPLE 10

Improvement in SPIA Activity of Antibody Adsorbed on TTC Coated Gold Sol

One hundred ml of gold sol was prepared as in Example 1 and the pH was adjusted to 9.0 Two and one-half milliliters of 2 mg/ml of the human anti-HIV (GC-143) in 10 mM CHES, pH 9.0 was added with stirring and the mixture was allowed to set at ambient temperature for approximately 2 hours with occasional swirling. Five ml of 1 mg/ml nonfat dry milk was added to the mixture with stirring and the mixture was allowed to set at ambient temperature for an additional hour. The coated sol was centrifuged at 2000×g for 15 minutes at ambient temperature and resuspended in 10 mM CHES, 0.5% BSA, 300 mM mannitol, 0.01% sodium azide, at pH 9.0. The centrifugation and resuspension step was repeated 3 times. The sol was finally resuspended in the same buffer and stored at 4° C. prior to use. A TTC coated sol prepared as in Example 9 was diluted with 10 mM CHES at pH 9.0 to obtain 60 ml of sol with an optical density of 2.0, the same approximate optical density of the gold sol prepared in Example 1. Six ml of 0.5 mg/ml human anti-HIV dissolved in 10 mM CHES, pH 9.0 was added with stirring and the mixture was allowed to set at ambient temperature for 1 hour, then overnight at 4° C. Six ml of 1 mg/ml nonfat dry milk was added with stirring and the mixture was allowed to set at ambient temperature for 1 hour. The coated sol was harvested as above and stored identically.

Figure 5:
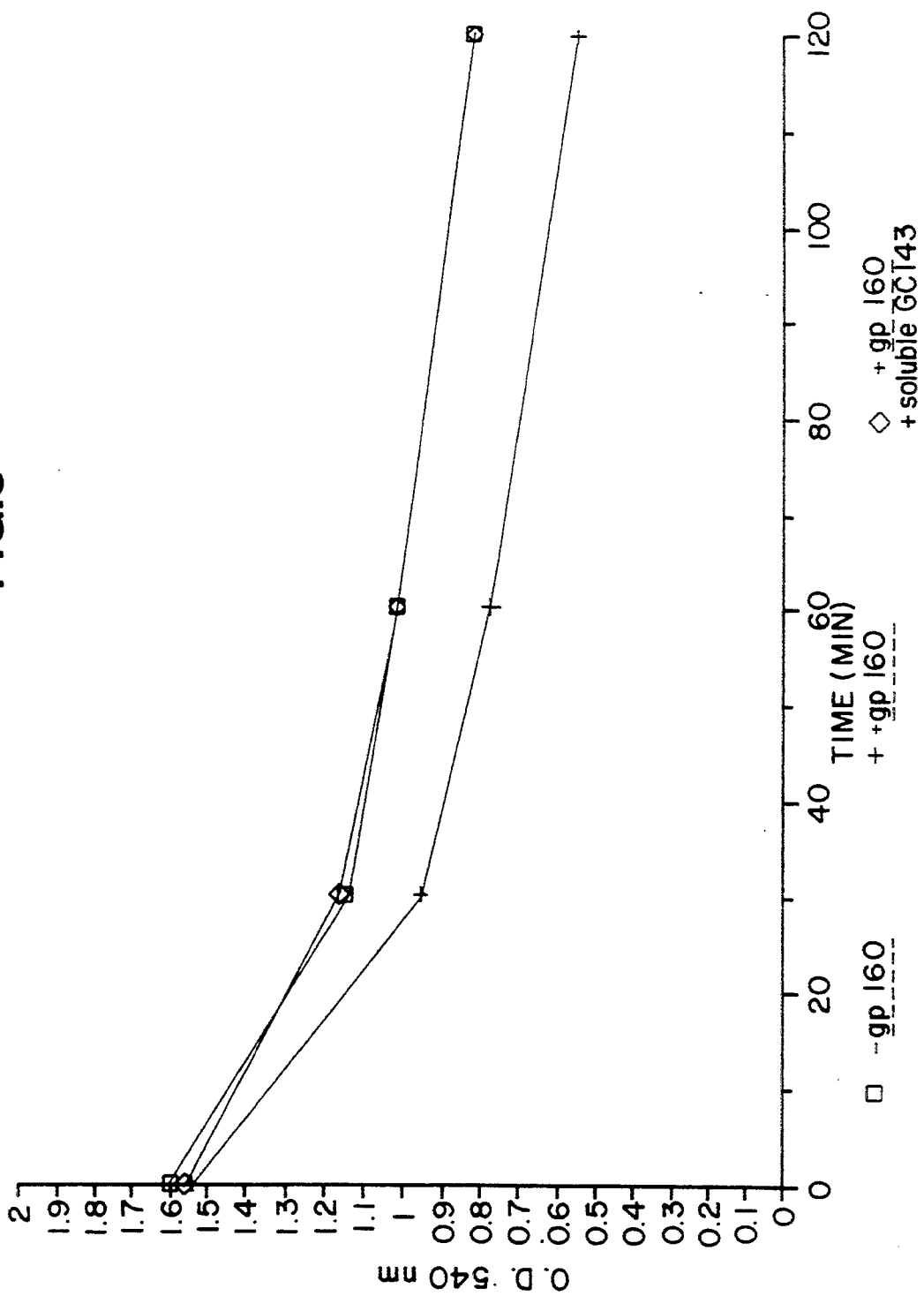
FIG. 5 shows the immunological activity and specificity of GC-143 adsorbed on a gold sol in a SPIA assay.
Figure 6:
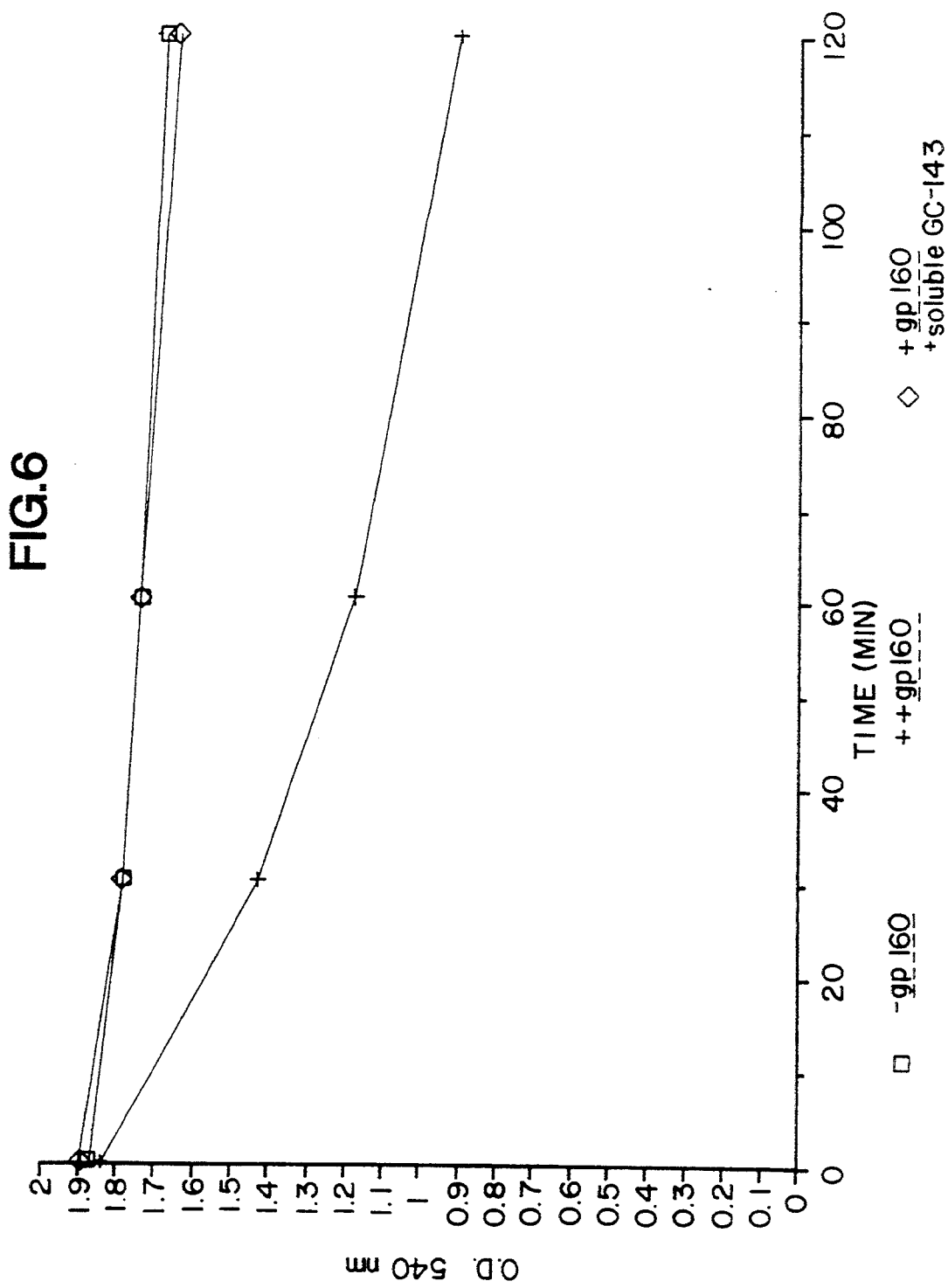
FIG. 6 shows the immunological activity and specificity of GC-143 adsorbed on a TTC coated gold sol in a SPIA assay.

Aliquots of each sol were diluted to an optical density at 540 nm of 2.0 with 0.1M MOPSO, 0.15M NaCl, 1% PEG 8000, 0.25% BSA, at pH 7.0. To replicate aliquots of each diluted sol were added a) one hundred μl buffer, b) one hundred μl of 10 μg/ml HIV gp160, or c) one hundred μl of a mixture of 5 μg/ml HIV gp160 and 5 μg/ml human anti-HIV which had been pre-incubated for 90 minutes at ambient temperature, as shown in FIGS. 5 and 6.

It is apparent that the GC-143 TTC coated sol is more immunologically active than its uncoated sol counterpart and that its use in the SPIA assay results in a more sensitive assay. Therefore, by functional criteria as well, the GC-143 TTC coated sol is also better than the uncoated sol counterpart.

EXAMPLE 11

Thiolation of Monoclonal Anti-HIV p24 using N-succinimidyl-S-acetylthioacetate (SATA)

One ml of monoclonal anti-HIV p24 at 1.46 mg/ml in 50 mM NAPO4, 1 mM ethylenediamine tetraacetic acid (EDTA), pH 7.5 was mixed with 0.02 ml of 5 mg/ml SATA in dimethylsulfoxide (DMSO) and allowed to react at ambient temperature for 2 hours. The reacted antibody was separated from the reaction components by gel filtration through a desalting column in the same buffer. One quarter mg of the reacted gel filtered antibody was diluted to 1 ml with the same buffer and 100 μl of 0.05M NaPO4, 25 mM EDTA, 0.5M NH2OH.HCl, at pH 7.5 was added with mixing. The reaction was allowed to set for 1.5 hours at ambient temperature. The deprotected antibody was gel filtered through a desairing column into the original buffer to remove unreacted reagents.

EXAMPLE 12

Improvement of Coating Properties of Thiolated Monoclonal Anti-HIV p24

Gold sol was prepared as described in Example 1 except that separate aliquots of the sol were adjusted to pH 6, 7, 8 and 9 with $K_2CO_3$. In parallel, separate aliquots of the underivatized and derivatized monoclonal anti-HIV p24 (see Example 11) were adjusted to 250, 200, 150, 100 and 50 μg/ml. For each of the above, the relative ability of derivatized and underivatized antibody to protect the gold sol from salt-induced agglomeration was made exactly as described in Example 9 (see FIGS. 7 and 8).

It is apparent from FIGS. 7 and 8 that the thiolation of this monoclonal antibody resulted in improved coating characteristics as judged by a) the fact that the derivatized antibody did not spontaneously agglomerate the sol, b) the decreased dependence of antibody protection against sol agglomeration on pH, and c) the lower relative amounts of derivatized antibody required to protect from salt-induced sol agglomeration in the presence of salt as compared to the underivatized antibody sol.

We claim:

1. A process for coating gold sol microparticles comprising:
   a) mixing gold sol microparticles with an alcohol solution of at least one compound selected from the group consisting of alkanethiol, di-thiol and tri-thiol compounds thereby producing coated gold sol microparticles;
   b) centrifuging said coated gold sol microparticles; and
   c) resuspending the coated gold sol microparticles in buffer.

2. A process for coating gold sol microparticles according to claim 1, wherein said alcohol solution additionally contains surfactant.

3. A process for attaching a binding moiety to gold sol microparticles comprising:
   a) coating said gold sol microparticles according to claim 1 to produce coated gold sol microparticles;
   b) incubating said coated gold sol microparticles and binding moiety to attach the binding moiety to said coated sol microparticles;
   c) blocking nonspecific sites on the coated gold sol microparticles of step b;
   d) centrifuging said coated gold sol microparticles of step c; and
   e) resuspending the coated gold sol microparticles of step d in buffer.

4. A process for attaching a binding moiety to gold sol microparticles comprising:
   a) coating gold sol microparticles according to the process of claim 2;
   b) incubating a mixture of the gold sol microparticles, appropriate chemical crosslinkers and binding moiety to attach the binding moiety to the coated gold sol microparticles;
   c) quenching said mixture;
   d) blocking nonspecific sites on the coated gold sol microparticles of step b;
   e) centrifuging the coated gold sol microparticles of step d; and
   f) resuspending in buffer.

5. A process for attaching a binding moiety to gold sol microparticles comprising:
   a) coating gold sol microparticles according to the process of claim 2;
   b) incubating said coated gold sol microparticles with a binding moiety;
   c) blocking nonspecific sites on said coated gold sol microparticles of step b;
   d) centrifuging said coated gold sol microparticles of step c;
   e) resuspending said gold sol microparticles of step d in buffer.

6. A process for attaching a binding moiety to gold sol microparticles comprising:

a) modifying said binding moiety by chemical thiolation;

b) incubating the thiolated binding moiety of step a with gold sol microparticles;

c) blocking nonspecific sites on the gold sol microparticles of step b;

d) centrifuging the gold sol microparticles of step c; and e) resuspending the gold sol microparticles of step d in the buffer.

* * * * *